(12) United States Patent
Lant et al.

(10) Patent No.: US 10,336,970 B2
(45) Date of Patent: *Jul. 2, 2019

(54) LIQUID DETERGENT COMPOSITION COMPRISING AN ENCAPSULATED ENZYME

(71) Applicant: The Procter & Gamble Company, Cincinnati, OH (US)

(72) Inventors: Neil Joseph Lant, Newcastle lupon Tyne (GB); Steven George Patterson, Newcastle upon Tyne (GB); Nazarmohammad Gulamhussain Momin, Newcastle upon Tyne (GB); Jordan Courtney Toye, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,440

(22) Filed: Apr. 11, 2017

(65) Prior Publication Data

US 2017/0335244 A1 Nov. 23, 2017

(30) Foreign Application Priority Data

May 23, 2016 (EP) ..................................... 16170848
Mar. 24, 2017 (EP) ..................................... 17162876

(51) Int. Cl.
| | |
|---|---|
| *C11D 3/386* | (2006.01) |
| *C11D 17/04* | (2006.01) |
| *C11D 17/00* | (2006.01) |
| *C11D 11/00* | (2006.01) |
| *C11D 3/50* | (2006.01) |
| *C11D 1/22* | (2006.01) |
| *C11D 1/29* | (2006.01) |
| *C11D 1/66* | (2006.01) |
| *C11D 1/83* | (2006.01) |
| *C11D 3/37* | (2006.01) |
| *C11D 3/382* | (2006.01) |
| *C12N 9/16* | (2006.01) |
| *C11D 1/72* | (2006.01) |

(52) U.S. Cl.
CPC ............ *C11D 3/38627* (2013.01); *C11D 1/22* (2013.01); *C11D 1/29* (2013.01); *C11D 1/66* (2013.01); *C11D 1/83* (2013.01); *C11D 3/3715* (2013.01); *C11D 3/3753* (2013.01); *C11D 3/382* (2013.01); *C11D 3/38672* (2013.01); *C11D 3/50* (2013.01); *C11D 11/0017* (2013.01); *C11D 11/0023* (2013.01); *C11D 17/0039* (2013.01); *C11D 17/042* (2013.01); *C11D 17/043* (2013.01); *C12N 9/16* (2013.01); *C12Y 301/00* (2013.01); *C11D 1/72* (2013.01)

(58) Field of Classification Search
None
See application file for complete search history.

(56) References Cited

U.S. PATENT DOCUMENTS 9,029,310 B2    5/2015 Maas et al.

FOREIGN PATENT DOCUMENTS

| WO | WO 93/22417 A1 | 11/1993 |
| WO | WO2010003934 | * 1/2010 |
| WO | WO 2016/023685 A1 | 2/2016 |

OTHER PUBLICATIONS

Keen et al. Langmuir (2014), 30(8), 1939-1948.*
European Search Report for Application No. 16170848.2-1375, dated Nov. 22, 2016, 9 pages.
PCT Search Report for appl. No. PCT/US2017/033732, dated Aug. 21, 2017, 14 pages.

* cited by examiner

*Primary Examiner* — Christian L Fronda
(74) *Attorney, Agent, or Firm* — Gregory S. Darley-Emerson

(57) ABSTRACT

Liquid detergent composition that includes encapsulated enzymes. Related uses and methods.

19 Claims, No Drawings

LIQUID DETERGENT COMPOSITION COMPRISING AN ENCAPSULATED ENZYME

FIELD OF THE INVENTION

The present disclosure relates to liquid detergent composition comprising encapsulated enzymes and uses thereof.

BACKGROUND OF THE INVENTION

Enzymes are often used by formulators in liquid detergent compositions to provide various cleaning and/or care benefits. However, in some instances, other detergent ingredients can act as substrates for enzymes formulated into the detergent composition, which results in these ingredients being broken down by the enzymes. This can negatively affect the cleaning or care ability of the detergent composition which in turn negatively affects the cleaning experience by the consumer.

This incompatibility can be overcome by encapsulating the enzyme. However, there is a tendency for the encapsulates to leak enzymes into the liquid detergent composition. Attempts in the art have focused on means to reduce the level of leakage from the encapsulate however the problem still persists.

There is a need in the art for a liquid detergent composition comprising an encapsulated enzyme wherein the negative impact of enzyme that has leaked from the encapsulate is minimized, whilst still providing a liquid detergent composition that provides effective cleaning and into which the encapsulated enzyme can be formulated.

It was surprisingly found that the liquid detergent composition of the present disclosure overcame this technical problem.

SUMMARY OF THE INVENTION

The present disclosure relates to a water-soluble unit dose article comprising a water-soluble film and a liquid detergent composition comprising between 25% and 55% by weight of the liquid detergent composition of a non-soap surfactant, wherein the non-soap surfactant comprises an anionic surfactant and a non-ionic surfactant and wherein the weight ratio of anionic surfactant to non-ionic surfactant is between 25:1 to 1:1.5; and wherein the liquid detergent composition comprises an encapsulated enzyme.

The present disclosure also relates to the use of a liquid detergent composition comprising between 25% and 55% by weight of the liquid detergent composition of a non-soap surfactant, wherein the non-soap surfactant comprises an anionic surfactant and a non-ionic surfactant and wherein the ratio of anionic surfactant to non-ionic surfactant is between 25:1 to 1:1.5 to minimise the level of enzyme contamination in said liquid detergent composition that has leaked from encapsulates present in said liquid detergent composition.

DETAILED DESCRIPTION OF THE INVENTION

Liquid Detergent Composition

The composition of the present disclosure is a liquid detergent composition. The term 'liquid detergent composition' refers to any detergent composition comprising a liquid capable of wetting and treating an item or surface e.g., cleaning clothing in a domestic washing machine, and includes, but is not limited to, liquids, gels, pastes, dispersions and the like. The liquid composition can include solids or gases in suitably subdivided form, but the liquid composition excludes forms which are non-fluid overall, such as tablets or granules.

The liquid composition may be formulated into a unit dose article. The unit dose article of the present disclosure comprises a water-soluble film which fully encloses the liquid composition in at least one compartment. Suitable unit dose articles are described in more detail below.

The liquid detergent composition may be a liquid laundry detergent composition, an automatic dishwashing detergent, a hand dish detergent, a hard surface cleaner or a mixture thereof, preferably wherein the liquid detergent is a liquid laundry detergent composition.

The liquid detergent composition can be used as a fully formulated consumer product, or may be added to one or more further ingredient to form a fully formulated consumer product.

The liquid detergent composition may be a 'pre-treat' composition which is added to a fabric, preferably a fabric stain, ahead of the fabric being added to a wash liquor.

The liquid detergent composition can be used in a fabric hand wash operation or may be used in an automatic machine fabric wash operation.

The liquid detergent composition of the present disclosure comprises between 25% and 55% by weight of the liquid detergent composition of a non-soap surfactant, wherein the non-soap surfactant comprises an anionic surfactant and a non-ionic surfactant and wherein the weight ratio of anionic surfactant to non-ionic surfactant is from 25:1 to 1:1.5. The non-soap surfactant is described in more detail below.

The liquid detergent composition comprises an encapsulated enzyme. The encapsulated enzyme is described in more detail below.

The liquid detergent composition may comprise between 0.5% and 50%, preferably between 0.5% and 40%, more preferably between 0.5% and 30%, more preferably between 0.5% and 25%, even more preferably between 1% and 20%, most preferably between 2% and 15% by weight of the liquid detergent composition of water.

The liquid detergent composition may comprise hydrogenated castor oil, perfume esters, terphthalate polymer or a mixture thereof. The hydrogenated castor oil and perfume esters are described in more detail below.

The liquid detergent may comprise an adjunct ingredient preferably selected from hueing dyes, polymers, surfactants, builders, dye transfer inhibiting agents, dispersants, enzymes, enzyme stabilizers, catalytic materials, bleach activators, polymeric dispersing agents, anti-redeposition agents, suds suppressors, aesthetic dyes, opacifiers, perfumes, perfume delivery systems, structurants, hydrotropes, processing aids, pigments and mixtures thereof.

Without wishing to be bound by theory, attempts to reduce the negative impact of leaked enzyme on other ingredients in the detergent composition have focused on reducing the amount of leakage from the encapsulate. The present disclosure addresses the problem by formulating a detergent composition comprising an encapsulated enzyme but whereby any leaked enzyme is denatured by the liquid detergent composition. However, the detergent composition is such that the enzyme is not denatured when in the encapsulate and is still available to provide cleaning or care benefits upon use. Furthermore, the detergent composition overall still provides effective cleaning and/or care benefits. Without wishing to be bound by theory it was found that the specific level and ratio of the non-soap surfactant of the present disclosure achieved this.

Non-Soap Surfactant

The liquid detergent composition of the present disclosure comprises between 25% and 55%, preferably between 30% and 50%, more preferably between 35% and 48% by weight of the liquid detergent composition of a non-soap surfactant.

By non-soap surfactant we here mean a surfactant that is not a soap or neutralized fatty acid.

The non-soap surfactant comprises an anionic surfactant and a non-ionic surfactant. The anionic surfactant and the non-ionic surfactant are described in more detail below.

The weight ratio of anionic surfactant to non-ionic surfactant is from 25:1 to 1:1.5, preferably from 23:1 to 2.5:1, more preferably from 20:1 to 5:1, most preferably from 18:1 and 10:1.

Alternatively, the weight ratio of anionic surfactant to non-ionic surfactant may be from 5:1 to 1:5, preferably from 2.5:1 to 1:2.5, more preferably from 1.5:1 to 1:1.5.

Anionic Surfactant

The non-soap surfactant comprises an anionic surfactant. Preferably, the anionic surfactant is selected from linear alkylbenzene sulphonate, alkoxylated alkyl sulfate, or a mixture thereof.

Exemplary anionic surfactants are the alkali metal salts of $C_{10}$-$C_{16}$ alkyl benzene sulfonic acids, or $C_{11}$-$C_{14}$ alkyl benzene sulfonic acids. In one aspect, the alkyl group is linear and such linear alkyl benzene sulfonates are known as "LAS". Alkyl benzene sulfonates, and particularly LAS, are well known in the art. Especially useful are the sodium, potassium and amine linear straight chain alkylbenzene sulfonates in which the average number of carbon atoms in the alkyl group is from about 11 to 14.

Specific, non-limiting examples of anionic surfactants useful herein include the acid or salt forms of: a) $C_{11}$-$C_{18}$ alkyl benzene sulfonates (LAS); b) $C_{10}$-$C_{20}$ primary, branched-chain and random alkyl sulfates (AS), including predominantly $C_{12}$ alkyl sulfates; c) $C_{10}$-$C_{18}$ secondary (2,3) alkyl sulfates with non-limiting examples of suitable cations including sodium, potassium, ammonium, amine and mixtures thereof; d) $C_{10}$-$C_{18}$ alkyl alkoxy sulfates ($AE_xS$) wherein x is from 1-30; e) $C_{10}$-$C_{18}$ alkyl alkoxy carboxylates in one aspect, comprising 1-5 ethoxy units; f) mid-chain branched alkyl sulfates; g) mid-chain branched alkyl alkoxy sulfates; h) modified alkylbenzene sulfonate; i) methyl ester sulfonate (MES); and j) alpha-olefin sulfonate (AOS).

Non-Ionic Surfactant

The non-soap surfactant comprises a non-ionic surfactant. Preferably, the non-ionic surfactant is selected from fatty alcohol alkoxylate, an oxo-synthesised fatty alcohol alkoxylate, Guerbet alcohol alkoxylates, alkyl phenol alcohol alkoxylates or a mixture thereof.

The nonionic surfactant may comprise an ethoxylated nonionic surfactant. The ethoxylated nonionic surfactant may be, e.g., primary and secondary alcohol ethoxylates, especially the $C_8$-$C_{20}$ aliphatic alcohols ethoxylated with an average of from 1 to 50 or even 20 moles of ethylene oxide per mole of alcohol, and more especially the $C_{10}$-$C_{15}$ primary and secondary aliphatic alcohols ethoxylated with an average of from 1 to 10 moles of ethylene oxide per mole of alcohol.

The ethoxylated alcohol non-ionic surfactant can be, for example, a condensation product of from 3 to 8 mol of ethylene oxide with 1 mol of a primary alcohol having from 9 to 15 carbon atoms.

The non-ionic surfactant may comprise a fatty alcohol ethoxylate of formula $RO(EO)_nH$, wherein R represents an alkyl chain between 4 and 30 carbon atoms, (EO) represents one unit of ethylene oxide monomer and n has an average value between 0.5 and 20.

Encapsulated Enzyme

The liquid detergent composition comprises an encapsulated enzyme. By encapsulated, we herein mean that the enzyme is immobilized within a particle or the like and is not 'free' within the liquid detergent composition.

The encapsulated enzyme may be of the core-shell type, absorbed onto or into a matrix or a mixture thereof, preferably the encapsulated enzyme is of the core-shell type. A core-shell particle is one comprising an outer shell that surrounds a core, wherein the enzyme is comprised within the core.

When in encapsulated form the enzymes are typically encapsulated in a polymeric material. Methods of encapsulation of the enzymes are for example, by spray-drying a liquid composition containing the enzyme(s) and the polymer(s), or by drying a liquid composition containing the enzyme and polymer, or by emulsion polymerisation, co-acervation, precipitation or interfacial polymerisation optionally in the presence of the enzyme, optionally followed by drying and/or size reduction processes. Suitable polymers for encapsulating enzymes include: polyvinyl alcohol, polyvinylpyrrolidone, carboxymethylcellulose, guar gum, polycarboxylic acid, methylcellulose, hydroxypropyl methylcellulose, proteins, polybranched polyamines, such as polyethyleneimines (PEI), (hydrophobically modified) polysaccharide modified cellulosic polymers, derivatives or co-polymers thereof and mixtures thereof. Examples of modified cellulosic polymers include hydroxypropyl methylcellulose phthalate, cellulose acetate phthalate Examples of modified gums include modified guar gum, gum benzoin, gum tragacanth, gum arabic and gum acacia. Examples of modified proteins are modified casein, gelatin and albumin. Examples of modified polymers may be selected from copolymers of at least one hydrophobic vinylic monomer with a least one hydrophilic vinylic monomer. Suitable hydrophilic vinylic monomer is vinylpyrrolidone. Suitable hydrophobic vinylic monomer is C1-C18 alkyl acrylates, C1-C18 alkyl methacrylates, C3-C18 cycloalkyl acrylates, C3-C18 cycloalkyl methacrylates and vinyl C1-C18 alkanoates and mixtures thereof. The polymer may comprise a polymer selected from homo- and copolymers having a C—C-backbone, wherein the C—C-backbone carries carboxyl groups, which may be present in the acidic form or in the neutralized form, and wherein the C—C-backbone comprises at least 20% by weight, e.g. from 20 to 98% by weight, based on the total weight of the polymer (i.e. based on the total weight of repeating units in the polymer P), of hydrophobic repeating units. The polymer may comprise branching, for example branched copolymer matrix particles formed from vinyl pyrrolidone and vinyl acetate. The polymer may comprise a copolymers, for example as described in WO2010/003934, based on maleic acid or (meth) acrylic acid. The polymer may be cross-linked.

Preferred polymers have a molecular weight from 1000 to 500,000, or 2000 to 200000 Dalton weight average. Typically the weight ratio of enzyme to polymer is from 1:50 to 10:1.

The polymer may be selected to be substantially soluble in an aqueous solution having an ionic strength of 0 mol/kg and insoluble in an aqueous solution having an ionic strength of more than 1 mol/kg, for example in which the polymer comprises 35-95% w/w of hydrophilic monomer units, based on the total weight of the polymer.

Hydrophobically modified polyvinyl alcohol or hydrophobically modified polyvinyl pyrrolidone may be preferred, optionally with high levels of hydrolysis, greater than 60%, or even greater than 80 or 90%. Suitable hydrophobic modifying groups include keto-ester and/or butyryl groups and mixtures thereof and preferably the total degree of substitution (DS) is between about 3% and 20%.

The fatty acid decarboxylase enzyme, when present in an additive particle may be the only enzyme in the additive particle or may be present in the additive particle in combination with one or more additional enzymes.

Preferably, the shell material comprises a polymeric material, preferably selected from polyvinyl alcohol, polyvinylpyrrolidone, carboxymethylcellulose, guar gum, polycarboxylic acid, methylcellulose, hydroxypropyl methylcellulose, proteins, polybranched polyamines, such as polyethyleneimines (PEI), (hydrophobically modified) polysaccharide modified cellulosic polymers, derivatives or co-polymers thereof and mixtures thereof.

Preferably, the liquid detergent composition comprises between 0.0001% and 0.75%, preferably between 0.0005% and 0.5%, more preferably between 0.001% and 0.5% by weight of the liquid laundry detergent composition of the encapsulated enzyme. Herein we mean that the weight percentage of the enzyme protein only excluding the weight percentage of any other materials such as the shell that may be present in the encapsulate and 'encapsulated enzyme' refers to the enzyme present in the encapsulate as opposed to any other enzyme that may be present in the liquid detergent composition.

Preferably, the enzyme is selected from the group comprising hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof, preferably wherein the enzyme is a lipase, a cellulase or a mixture thereof, most preferably wherein the enzyme is a lipase.

Hydrogenated Castor Oil

Hydrogenated castor oil (HCO) as used herein most generally can be any hydrogenated castor oil or derivative thereof, provided that it is capable of crystallizing in the liquid laundry detergent composition. Castor oils may include glycerides, especially triglycerides, comprising $C_{10}$ to $C_{22}$ alkyl or alkenyl moieties which incorporate a hydroxyl group. Hydrogenation of castor oil, to make HCO, converts the double bonds which may be present in the starting oil as ricinoleyl moieties. As such, the ricinoleyl moieties are converted into saturated hydroxyalkyl moieties, e.g., hydroxystearyl. The HCO herein may be selected from: trihydroxystearin; dihydroxystearin; and mixtures thereof. The HCO may be processed in any suitable starting form, including, but not limited to those selected from solid, molten and mixtures thereof. The corresponding percentage of hydrogenated castor oil delivered into a finished laundry detergent product may be below 1.0%, typically from 0.1% to 0.8%. HCO may be present at a level of between 0.01% and 1%, or even between 0.05% and 0.8% by weight of the liquid laundry detergent composition.

HCO of use in the present disclosure includes those that are commercially available. Non-limiting examples Elementis, Plc.

Perfume Ester

Perfume esters are perfume raw materials wherein the perfume raw material comprises an ester. Those skilled in the art will be aware of suitable materials.

Polyester Terephthalate Polymer

The polymer comprises a polyester terephthalate backbone grafted with one or more anionic or non-ionic groups. Suitable polymers have a structure as defined by one of the following structures (I), (II) or (III):

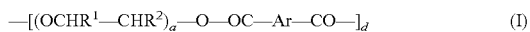  (I)

  (II)

  (III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group. Suitable soil release polymers are sold by Clariant under the TexCare® series of polymers, e.g. TexCare® SRN240 and TexCare® SRA300. Other suitable soil release polymers are sold by Solvay under the Repel-o-Tex® series of polymers, e.g. Repel-o-Tex® SF2 and Repel-o-Tex® Crystal.

Water-Soluble Unit Dose Article

The present disclosure is to a water-soluble unit dose article comprising a water-soluble film and a liquid detergent composition according to the present disclosure.

The water-soluble unit dose article comprises at least one water-soluble film shaped such that the unit-dose article comprises at least one internal compartment surrounded by the water-soluble film. The at least one compartment comprises the liquid laundry detergent composition. The water-soluble film is sealed such that the liquid laundry detergent composition does not leak out of the compartment during storage. However, upon addition of the water-soluble unit dose article to water, the water-soluble film dissolves and releases the contents of the internal compartment into the wash liquor.

The compartment should be understood as meaning a closed internal space within the unit dose article, which holds the liquid laundry detergent. Preferably, the unit dose article comprises a water-soluble film. The unit dose article is manufactured such that the water-soluble film completely surrounds the liquid laundry detergent composition and in doing so defines the compartment in which the liquid laundry detergent resides. The unit dose article may comprise two films. A first film may be shaped to comprise an open compartment into which the liquid laundry detergent is added. A second film is then laid over the first film in such an orientation as to close the opening of the compartment. The first and second films are then sealed together along a seal region. The water-soluble film is described in more detail below.

The unit dose article may comprise more than one compartment, even at least two compartments, or even at least three compartments. The compartments may be arranged in superposed orientation, i.e. one positioned on top of the other. Alternatively, the compartments may be positioned in a side-by-side orientation, i.e. one orientated next to the other. The compartments may even be orientated in a 'tyre and rim' arrangement, i.e. a first compartment is positioned next to a second compartment, but the first compartment at least partially surrounds the second compartment, but does not completely enclose the second compartment. Alternatively one compartment may be completely enclosed within another compartment.

Wherein the unit dose article comprises at least two compartments, one of the compartments may be smaller than the other compartment. Wherein the unit dose article comprises at least three compartments, two of the compartments may be smaller than the third compartment, and preferably the smaller compartments are superposed on the larger compartment. The superposed compartments preferably are orientated side-by-side.

In a multi-compartment orientation, the liquid laundry detergent according to the present disclosure may be comprised in at least one of the compartments. It may for example be comprised in just one compartment, or may be comprised in two compartments, or even in three compartments.

Each compartment may comprise the same or different compositions. The different compositions could all be in the same form, or they may be in different forms.

The water-soluble unit dose article may comprise at least two internal compartments, wherein the liquid laundry detergent composition is comprised in at least one of the compartments, preferably wherein the unit dose article comprises at least three compartments, wherein the liquid laundry detergent composition is comprised in at least one of the compartments.

Water-Soluble Film

The film of the present disclosure is soluble or dispersible in water and comprises at least one polyvinylalcohol or a copolymer thereof. Preferably, the water-soluble film comprises a blend of at least two different polyvinylalcohol homopolymers, at least two different polyvinylalcohol copolymers, at least one polyvinylalcohol homopolymer and at least one polyvinylalcohol copolymer or a combination thereof.

The water-soluble film preferably has a thickness of from 20 to 150 micron, preferably 35 to 125 micron, even more preferably 50 to 110 micron, most preferably from about 70 to 90 microns especially about 76 micron. By film thickness, we herein mean the thickness of the film prior to any deformation during manufacture.

Preferably, the film has a water-solubility of at least 50%, preferably at least 75% or even at least 95%, as measured by the method set out here after using a glass-filter with a maximum pore size of 20 microns:

5 grams±0.1 gram of film material is added in a pre-weighed 3 L beaker and 2 L±5 ml of distilled water is added. This is stirred vigorously on a magnetic stirrer, Labline model No. 1250 or equivalent and 5 cm magnetic stirrer, set at 600 rpm, for 30 minutes at 30° C. Then, the mixture is filtered through a folded qualitative sintered-glass filter with a pore size as defined above (max. 20 micron). The water is dried off from the collected filtrate by any conventional method, and the weight of the remaining material is determined (which is the dissolved or dispersed fraction). Then, the percentage solubility or dispersability can be calculated.

Preferred film materials are preferably polymeric materials. The film material can, for example, be obtained by casting, blow-moulding, extrusion or blown extrusion of the polymeric material, as known in the art.

Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000.

Preferably, the water-soluble unit dose article comprises polyvinylalcohol.

Mixtures of polymers can also be used as the pouch material. This can be beneficial to control the mechanical and/or dissolution properties of the compartments or pouch, depending on the application thereof and the required needs. Suitable mixtures include for example mixtures wherein one polymer has a higher water-solubility than another polymer, and/or one polymer has a higher mechanical strength than another polymer. Also suitable are mixtures of polymers having different weight average molecular weights, for example a mixture of PVA or a copolymer thereof of a weight average molecular weight of about 10,000-40,000, preferably around 20,000, and of PVA or copolymer thereof, with a weight average molecular weight of about 100,000 to 300,000, preferably around 150,000. Also suitable herein are polymer blend compositions, for example comprising hydrolytically degradable and water-soluble polymer blends such as polylactide and polyvinyl alcohol, obtained by mixing polylactide and polyvinyl alcohol, typically comprising about 1-35% by weight polylactide and about 65% to 99% by weight polyvinyl alcohol.

Preferred for use herein are PVA polymers which are from about 60% to about 98% hydrolysed, preferably about 80% to about 90% hydrolysed, to improve the dissolution characteristics of the material.

Preferred films exhibit good dissolution in cold water, meaning unheated distilled water. Preferably such films exhibit good dissolution at temperatures of 24° C., even more preferably at 10° C. By good dissolution it is meant that the film exhibits water-solubility of at least 50%, preferably at least 75% or even at least 95%, as measured by the method set out here after using a glass-filter with a maximum pore size of 20 microns, described above.

Preferred films are those supplied by Monosol.

Of the total PVA resin content in the film described herein, the PVA resin can comprise about 30 to about 85 wt % of the first PVA polymer, or about 45 to about 55 wt % of the first PVA polymer. For example, the PVA resin can contain about 50 w. % of each PVA polymer, wherein the viscosity of the first PVA polymer is about 13 cP and the viscosity of the second PVA polymer is about 23 cP, measured as a 4% polymer solution in demineralized water at 20° C.

Preferably the film comprises a blend of at least two different polyvinylalcohol homopolymers and/or copolymers.

Most preferably the water soluble film comprises a blend of at least two different polyvinylalcohol homopolymers, especially a water soluble film comprising a blend of at least two different polyvinylalcohol homopolymers of different average molecular weight, especially a blend of 2 different polyvinylalcohol homopolymers having an absolute average viscosity difference $|\mu_2-\mu_1|$ for the first PVOH homopolymer and the second PVOH homopolymer, measured as a 4% polymer solution in demineralized water, in a range of 5 cP to about 15 cP, and both homopolymers having an average degree of hydrolysis between 85% and 95% preferably between 85% and 90%. The first homopolymer preferably has an average viscosity of 10 to 20 cP preferably 10 to 15 cP The second homopolymer preferably has an average viscosity of 20 to 30 cP preferably 20 to 25 cP. Most preferably the two homopolymers are blended in a 40/60 to a 60/40 weight % ratio.

Alternatively the water soluble film comprises a polymer blend comprising at least one copolymer comprising polyvinylalcohol and anionically modified monomer units. In particular the polymer blend might comprise a 90/10 to 50/50 weight % ratio of a polyvinylalcohol homopolymer and a copolymer comprising polyvinylalcohol and anionically modified monomer units. Alternatively the polymer blend might comprise a 90/10 to 10/90 weight % ratio of two different copolymers comprising polyvinylalcohol and anionically modified monomer units.

General classes of anionic monomer units which can be used for the PVOH corpolymer include the vinyl polymerization units corresponding to monocarboxylic acid vinyl monomers, their esters and anhydrides, dicarboxylic monomers having a polymerizable double bond, their esters and anhydrides, vinyl sulfonic acid monomers, and alkali metal salts of any of the foregoing. Examples of suitable anionic monomer units include the vinyl polymerization units corresponding to vinyl anionic monomers including vinyl acetic acid, maleic acid, monoalkyl maleate, dialkyl maleate, monomethyl maleate, dimethyl maleate, maleic anyhydride, fumaric acid, monoalkyl fumarate, dialkyl fumarate, monomethyl fumarate, dimethyl fumarate, fumaric anyhydride, itaconic acid, monomethyl itaconate, dimethyl itaconate, itaconic anhydride, vinyl sulfonic acid, allyl sulfonic acid, ethylene sulfonic acid, 2-acrylamido-1-methylpropanesulfonic acid, 2-acrylamido-2-methylpropanesulfonic acid, 2-methylacrylamido-2-methylpropanesulfonic acid, 2-sulfoethyl acrylate, alkali metal salts of the foregoing (e.g., sodium, potassium, or other alkali metal salts), esters of the foregoing (e.g., methyl, ethyl, or other $C_1$-$C_4$ or $C_6$ alkyl esters), and combinations thereof (e.g., multiple types of anionic monomers or equivalent forms of the same anionic monomer). In an aspect, the anionic monomer can be one or more acrylamido methylpropanesulfonic acids (e.g., 2-acrylamido-1-methylpropanesulfonic acid, 2-acrylamido-2-methylpropanesulfonic acid, 2-methylacrylamido-2-methylpropanesulfonic acid), alkali metal salts thereof (e.g., sodium salts), and combinations thereof. In an aspect, the anionic monomer can be one or more of monomethyl maleate, alkali metal salts thereof (e.g., sodium salts), and combinations thereof.

The level of incorporation of the one or more anionic monomer units in the PVOH copolymers is not particularly limited. In some aspects, the one or more anionic monomer units are present in a PVOH copolymer in an amount in a range of about 2 mol. % to about 10 mol. % (e.g., at least 2.0, 2.5, 3.0, 3.5, or 4.0 mol. % and/or up to about 3.0, 4.0, 4.5, 5.0, 6.0, 8.0, or 10 mol. % in various embodiments), individually or collectively.

Naturally, different film material and/or films of different thickness may be employed in making the compartments of the present disclosure. A benefit in selecting different films is that the resulting compartments may exhibit different solubility or release characteristics.

The film material herein can also comprise one or more additive ingredients. For example, it can be beneficial to add plasticisers, for example glycerol, ethylene glycol, diethyleneglycol, propylene glycol, dipropylene glycol, sorbitol and mixtures thereof. Other additives may include water and functional detergent additives, including surfactant, to be delivered to the wash water, for example organic polymeric dispersants, etc.

The film may be opaque, transparent or translucent. The film may comprise a printed area. The printed area may cover between 10 and 80% of the surface of the film; or between 10 and 80% of the surface of the film that is in contact with the internal space of the compartment; or between 10 and 80% of the surface of the film and between 10 and 80% of the surface of the compartment.

The area of print may cover an uninterrupted portion of the film or it may cover parts thereof, i.e. comprise smaller areas of print, the sum of which represents between 10 and 80% of the surface of the film or the surface of the film in contact with the internal space of the compartment or both.

The area of print may comprise inks, pigments, dyes, blueing agents or mixtures thereof. The area of print may be opaque, translucent or transparent.

The area of print may comprise a single colour or maybe comprise multiple colours, even three colours. The area of print may comprise white, black, blue, red colours, or a mixture thereof. The print may be present as a layer on the surface of the film or may at least partially penetrate into the film. The film will comprise a first side and a second side. The area of print may be present on either side of the film, or be present on both sides of the film. Alternatively, the area of print may be at least partially comprised within the film itself.

The area of print may comprise an ink, wherein the ink comprises a pigment. The ink for printing onto the film has preferably a desired dispersion grade in water. The ink may be of any color including white, red, and black. The ink may be a water-based ink comprising from 10% to 80% or from 20% to 60% or from 25% to 45% per weight of water. The ink may comprise from 20% to 90% or from 40% to 80% or from 50% to 75% per weight of solid.

The ink may have a viscosity measured at 20° C. with a shear rate of 1000 $s^{-1}$ between 1 and 600 cPs or between 50 and 350 cPs or between 100 and 300 cPs or between 150 and 250 cPs. The measurement may be obtained with a cone-plate geometry on a TA instruments AR-550 Rheometer.

The area of print may be achieved using standard techniques, such as flexographic printing or inkjet printing. Preferably, the area of print is achieved via flexographic printing, in which a film is printed, then moulded into the shape of an open compartment. This compartment is then filled with a detergent composition and a second film placed over the compartment and sealed to the first film. The area of print may be on either or both sides of the film.

Alternatively, an ink or pigment may be added during the manufacture of the film such that all or at least part of the film is coloured.

The film may comprise an aversive agent, for example a bittering agent. Suitable bittering agents include, but are not limited to, naringin, sucrose octaacetate, quinine hydrochloride, denatonium benzoate, or mixtures thereof. Any suitable level of aversive agent may be used in the film. Suitable levels include, but are not limited to, 1 to 5000 ppm, or even 100 to 2500 ppm, or even 250 to 2000 ppm.

Use of the Composition

The present disclosure relates to the use of the liquid detergent composition comprising between 25% and 55% by weight of the liquid detergent composition of a non-soap surfactant, wherein the non-soap surfactant comprises an anionic surfactant and a non-ionic surfactant and wherein the ratio of anionic surfactant to non-ionic surfactant is between 25:1 to 1:1.5 to minimise the level of enzyme contamination in said liquid detergent composition that has leaked from encapsulates present in said liquid detergent composition.

Process of Making

Those skilled in the art will be aware of processes to make the liquid detergent composition of the present disclosure. Those skilled in the art will be aware of standard processes and equipment to make the liquid detergent compositions.

Those skilled in the art will be aware of standard techniques to make the unit dose article. Standard forming processes including but not limited to thermoforming and vacuum forming techniques may be used.

A preferred method of making the water-soluble unit dose article according to the present disclosure comprises the steps of moulding a first water-soluble film in a mould to form an open cavity, filling the cavity with the liquid detergent composition, laying a second film over the first film to close the cavity, and sealing the first and second films together to produce the water-soluble unit dose article.

Process of Washing Fabrics

The present disclosure relates to a process of washing fabrics comprising the steps of contacting the liquid detergent composition or unit dose article of the present disclosure with water such that the liquid detergent composition is diluted in water by at least 400 fold to form a wash liquor, and contacting fabrics with said wash liquor.

The liquid detergent composition or unit dose article of the present disclosure can be added to a wash liquor to which laundry is already present, or to which laundry is added. The liquid detergent composition or unit dose article may be used in an automatic washing machine operation and added directly to the drum or to the dispenser drawer. The liquid detergent composition or unit dose article may be used in combination with other laundry detergent compositions such as fabric softeners or stain removers. The liquid detergent composition may be used as pre-treat composition in which it is added directly to a fabric, preferably a fabric stain, ahead of the wash operation.

EXAMPLES

The following test demonstrates that any enzyme free of the encapsulate is denatured by the liquid laundry detergent composition so minimising negative effects on other detergent ingredients. However, enzyme present in the encapsulate is not affected by the liquid laundry detergent composition within which the encapsulate resides.

The following liquid compositions were prepared;

| | |
|---|---|
| A | Liquid composition comprising 33 wt % non-soap anionic surfactant, 15.3 wt % non-ionic surfactant and other common laundry detergent ingredients up to 100 wt % |
| B | Formulation A + 0.6 ppm cellulose acetate phthalate (CAP) commercially available from Fluka encapsulated lipase (Lipex commercially available from Novozymes) |
| C | Formulation A + 0.3 ppm CAP encapsulated lipase + 0.3 ppm Lipex enzyme (non encapsulated) |
| D | Formulation A + 0.6 ppm Lipex enzyme (non encapsulated) |

Burnt beef stain swatches were prepared using 5 cm×5 cm knitted cotton (Warwick Equest), wherein 200 µL of burnt beef fat (Warwick Equest) was dosed onto each 5×5 cm swatch and stored at 25° C. for 3 days prior to use. Before being used stains were analysed on a Digieye apparatus (commercially available from Verivide) to obtain L*, a* and b* values.

Each test was repeated 4 times.

Four samples of each of the four compositions A-D were prepared and placed in an oven at 35° C. for 5 days. Following the 5 days, the compositions were diluted in a 1 L pot of water (xml composition added to 1 L water) and allowed to mix for 5 minutes. To this 49 g clean knitted cotton ballast (Warwick Equest) added along with 2× burnt beef stains, 2× lard stains and 12×SBL2004 swatches (CFT).

The swatches and ballast were then washed together with the diluted compositions as follows; Detergent dose: 2 g/L
Cycle: 25 min wash 30° C./1×5 min rinse 15° C.
Water hardness: City water 7.0 gpg Once the cycle was complete swatches were air dried overnight and L*, a* and b* values were obtained on the Digieye. The soil release index was then calculated as the different in L*, a* and b* values between the stained fabrics and the fabrics after washing. The higher the SRI, the bigger the difference seen in stain removal.

The ΔSRI was then calculated as the difference in SRI between Composition A and formulations B-D. The results can be seen in Tables 1 and 2.

TABLE 1

| Burnt Beef | AVRG SRI | ΔSRI | SE |
|---|---|---|---|
| Composition A | 68.48 | — | 1.087637 |
| Composition B | 75.15 | 6.67 | 0.837861 |
| Composition C | 72.95 | 4.47 | 0.682886 |
| Composition D | 70.14 | 1.65 | 1.670343 |

TABLE 2

| Lard | AVRG SRI | ΔSRI | SE |
|---|---|---|---|
| Composition A | 51.71 | 0.00 | 1.080033 |
| Composition B | 56.51 | 4.80 | 1.574079 |
| Composition C | 56.23 | 4.52 | 2.03962 |
| Composition D | 53.91 | 2.20 | 0.968002 |

As can be seen from Tables 1 and 2, the biggest ΔSRI was seen for Composition B which comprised just encapsulated enzyme. Composition C comprising some encapsulated enzyme and some non-encapsulated enzyme to simulate a scenario wherein some of the enzyme has leaked out of the encapsulate. In this case the ΔSRI is lower indicating the non-encapsulated enzyme has been denatured by the liquid composition within which it resides during storage over 5 days. Composition D has the lowest ΔSRI wherein no encapsulated enzyme is present. This confirms that the liquid composition has also denatured this higher concentration of non-encapsulated enzyme.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water-soluble unit dose article comprising a water-soluble film and a liquid detergent composition comprising between 25% and 55% by weight of the liquid detergent composition of a non-soap surfactant, wherein the non-soap surfactant comprises an anionic surfactant and a non-ionic surfactant and wherein the weight ratio of anionic surfactant to non-ionic surfactant is between 23:1 to 2.5:1; and
   wherein the liquid detergent composition comprises an encapsulated enzyme.

2. The water-soluble unit dose article according to claim 1, wherein the enzyme is selected from the group consisting of hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, amylases, and mixtures thereof.

3. The water-soluble unit dose article according to claim 2, wherein the enzyme is a lipase, a cellulose, or a mixture thereof.

4. The water-soluble unit dose article according to claim 3, wherein the enzyme is a lipase.

5. The water-soluble unit dose article according to claim 1, wherein the encapsulated enzyme is of the core-shell type, absorbed onto or into a matrix, or a mixture thereof.

6. The water-soluble unit dose article according to claim 5, wherein the encapsulated enzyme is of the core-shell type, wherein the enzyme is located within the core.

7. The water-soluble unit dose article according to claim 6, wherein the shell comprises a polymeric material selected from polyvinyl alcohol, polyvinylpyrrolidone, carboxymethylcellulose, guar gum, polycarboxylic acid, methylcellulose, hydroxypropyl methylcellulose, proteins, polybranched polyamines, cellulosic polymers, derivatives thereof, co-polymers thereof, and mixtures thereof.

8. The water-soluble unit dose article according to claim 1, wherein the liquid detergent composition comprises between 0.0001% and 0.75%, by weight of the liquid laundry detergent composition, of the encapsulated enzyme.

9. The water-soluble unit dose article according to claim 1, wherein the liquid detergent composition comprises between 30% and 50%, by weight of the liquid detergent composition, of the non-soap surfactant.

10. The water-soluble unit dose article according to claim 1, wherein the ratio of anionic surfactant to non-ionic surfactant is between 20:1 to 5:1.

11. The water-soluble unit dose article according to claim 10, wherein the ratio of anionic surfactant to non-ionic surfactant is between 18:1 and 10:1.

12. The water-soluble unit dose article according to claim 1, wherein the anionic surfactant is selected from linear alkylbenzene sulphonate, alkoxylated alkyl sulfate, or a mixture thereof.

13. The water-soluble unit dose article according to claim 1, wherein the non-ionic surfactant is selected from fatty alcohol alkoxylate, an oxo-synthesised fatty alcohol alkoxylate, Guerbet alcohol alkoxylates, alkyl phenol alcohol alkoxylates, or a mixture thereof.

14. The water-soluble unit dose article according to claim 1, wherein the liquid detergent composition comprises an adjunct ingredient selected from hueing dyes, polymers, surfactants, builders, dye transfer inhibiting agents, dispersants, enzymes, enzyme stabilizers, catalytic materials, bleach activators, polymeric dispersing agents, anti-redeposition agents, suds suppressors, aesthetic dyes, opacifiers, perfumes, perfume delivery systems, structurants, hydrotropes, processing aids, pigments, and mixtures thereof.

15. The water-soluble unit dose article according to claim 1, wherein the liquid detergent composition comprises between 1% and 20%, by weight of the liquid detergent composition, of water.

16. The water-soluble unit dose article according to claim 1, wherein the liquid detergent composition comprises hydrogenated castor oil, perfume esters, polyester terphthalate polymer, or a mixture thereof.

17. The water-soluble unit dose article according to claim 1, wherein the liquid detergent composition is a liquid laundry detergent composition, an automatic dishwashing detergent, a hand dish detergent, a hard surface cleaner or a mixture thereof.

18. The water-soluble unit dose article according to claim 1, wherein the water-soluble film comprises at least one polyvinylalcohol or a copolymer thereof.

19. A process of washing fabrics comprising the steps of:
   contacting the liquid detergent composition according to claim 1 with water such
   that the liquid detergent composition is diluted in water by at least 400-fold to form a wash liquor, and
   contacting fabrics with said wash liquor.

* * * * *